(12) United States Patent
Waldmann et al.

(10) Patent No.: US 6,271,345 B1
(45) Date of Patent: Aug. 7, 2001

(54) ENZYME CLEAVABLE LINKER BOUND TO SOLID PHASE FOR ORGANIC COMPOUND SYNTHESIS

(75) Inventors: Herbert Waldmann, Rheinzabern; Bernd Sauerbrei; Uwe Grether, both of Karlsruhe, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/214,100

(22) PCT Filed: Jun. 27, 1997

(86) PCT No.: PCT/EP97/03379

§ 371 Date: Dec. 28, 1998

§ 102(e) Date: Dec. 28, 1998

(87) PCT Pub. No.: WO98/01406

PCT Pub. Date: Jan. 15, 1998

(30) Foreign Application Priority Data

Jul. 3, 1996 (DE) ............................................. 196 26 762

(51) Int. Cl.[7] .......................... C07K 17/00; C07K 17/06; C12P 21/06; C12N 11/06
(52) U.S. Cl. ......................... 530/334; 435/68.1; 435/181; 530/402; 530/816
(58) Field of Search .................................... 435/68.1, 181; 530/334, 402, 816

(56) References Cited

U.S. PATENT DOCUMENTS

| 5,288,514 | 2/1994 | Ellman ...................................... 427/2 |
| 5,324,483 | 6/1994 | Cody et al. ........................... 422/131 |
| 5,369,017 | 11/1994 | Wong et al. ......................... 435/68.1 |
| 5,635,598 | * | 6/1997 | Lebl et al. ............................ 530/334 |

FOREIGN PATENT DOCUMENTS

| 92/00091 | 1/1992 | (WO) . |
| 95/16712 | 6/1995 | (WO) . |
| 95/30642 | 11/1995 | (WO) . |
| 96/00148 | 1/1996 | (WO) . |
| 96/00391 | 1/1996 | (WO) . |
| 97/20855 | 6/1997 | (WO) . |

OTHER PUBLICATIONS

Angew Chem. Int. ed. Engl. 18 (1979) No. 3, 221–222.
J. of Med. Chem. vol. 37, No. 9, Apr. 29, 1994, 1233–1251.
Int. J. Peptide Protein Res. 41, 1993, 201–203.
J. Am. Chem. Soc. vol. 116, No. 4, Feb. 23, 1994, 2661–2662.
J. Chem. Soc. Chem. Comm. No. 19, Oct. 7, 1995, 2163–2164.
The Combinatorial Chem. Catalog, Novabiochem Mar. 1998.
Tet Letrs. vol., 36, No. 7, 983–986, 1995.
J Am. Chem.Soc. 1994, 116, 1135–1136.
Resins for Solid Phase Org. Chem, Novabiochem, 1994, 1–26.
J Chem. Soc. Chem Comm. 1992, Band 14, 1033–4.
Angew. Chem. Int. Ed. Engl. 1995, 34 No. 20, 2259–2262.
Angew. Chem. 103, 1991, 117–133.
Angew. Chem. 1995, 107, Nr. 20 2425–2428.

* cited by examiner

Primary Examiner—David M. Naff
(74) Attorney, Agent, or Firm—Keil & Weinkauf

(57) ABSTRACT

An enzyme cleavable linker is prepared on which organic compounds are synthesized when the linker is bound to a solid phase. The linker contains a functional group on which a synthesized organic compound is bound when synthesis takes place, and a recognition site for a hydrolytic enzyme. Reacting the linker with the enzyme causes the linker to fragment at a site different from the recognition site to liberate the synthesized organic compound. The solid phase may be a crosslinked polyacrylamide containing an amino group for attaching the linker, and the linker is bound to the solid phase via a spacer. The spacer is attached to the solid phase by an ester, ether, amide or amine linkage, or a sulfide or phosphate linkage. In a specific reaction of forming a solid phase containing the linker, 2-acetoxy-5-hydroxymethylbenzoic acid is attached to an amino group-containing polymer via a spacer followed by conversion to a chloroformic ester.

6 Claims, No Drawings

ENZYME CLEAVABLE LINKER BOUND TO SOLID PHASE FOR ORGANIC COMPOUND SYNTHESIS

BACKGROUND OF THE INVENTION

1. Field of the Invention

The invention relates to enzymatically cleavable linkers for solid-phase syntheses, to a process for their preparation and to their use.

2. Description of the Related Art

A large number of molecular assay systems are being developed for modern research looking for active substances, such as receptor binding assays, enzyme assays and cell-cell interaction assays. Automation and miniaturization of these assay systems makes it possible to assay an increasingly large number of chemicals for their biological effect in random screening and thus form a possible use as lead structure for an active substance in medicine, veterinary medicine or crop protection.

This development has led to classical synthetic chemistry becoming the limiting factor in research looking for active substances.

If the efficiency of the developed assay systems is to be fully exploited there must be a considerable increase in the efficiency of chemical synthesis of active substances.

Combinatorial chemistry can contribute to this required increase in efficiency, especially when it makes use of automated solid-phase synthetic methods (see, for example, review articles in J. Med. Chem. 37 (1994), 1233 and 1385).

The principle of these combinatorial syntheses is based on reaction at every stage of the synthesis not just with one building block in the synthesis but with several, either in parallel or in a mixture. All possible combinations are formed at every stage, so that a large number of products, called a substance library, results after only a few stages with relatively few building blocks.

Solid-phase synthesis has the advantage that byproducts and excess reactants can easily be removed, so that elaborate purification of the products is unnecessary. Reaction rates can be increased, and conversions optimized, by large excesses of the dissolved reactant. The finished synthetic products can be passed directly, i.e. bound to the support, or after elimination from the solid phase to mass screening. Intermediates can also be tested in the mass screening.

Applications described hitherto are confined mainly to the peptide and nucleotide sectors (Lebl et al., Int. J. Pept. Prot. Res. 41, 1993: 203 and WO 92/00091) or their derivatives (WO 96/00391). Since peptides and nucleotides have only limited uses as drugs because of their unfavorable pharmacological properties, it is desirable to utilize the solid-phase synthetic methods known and proven in peptide and nucleotide chemistry for synthetic organic chemistry.

U.S. Pat. No. 5,288,514 reports one of the first combinatorial solid-phase syntheses in organic chemistry outside peptide and nucleotide chemistry. U.S. Pat. No. 5,288,514 describes the sequential solid-phase synthesis of 1,4-benzodiazepines.

WO 95/16712, WO 95/30642 and WO 96/00148 describe other solid-phase syntheses of potential active substances in combinatorial chemistry.

However, in order fully to utilize the possibilities of modern assay systems in mass screening, it is necessary continually to feed novel compounds with a maximum degree of structural diversity into the mass screening. This procedure makes it possible to reduce considerably the time taken to identify and optimize a novel lead structure for active substances.

It is therefore necessary continually to develop novel and diverse combinatorial solid-phase syntheses.

It is important for these novel syntheses that the individual building blocks in the solid-phase synthesis are optimally matched with one another. The choice of the solid phase, such as glass, ceramic or resins, and of the linker crucially influences the subsequent chemistry on the support.

In order to be able to carry out the widest possible range of organic syntheses on solid phases there is a considerable need for novel solid phases, and novel linker and anchor groups, to be developed.

Linker groups used hitherto are labile to bases or acids, and their elimination conditions are too drastic for many substances synthesized on the support. Great efforts are therefore being made to construct linkers which can be eliminated from the solid phase under milder conditions.

It would be desirable in this connection to be able to use enzymes for cleavage of the linkers under mild conditions, as is already possible in a few cases for protective groups. An example of an enzymatically cleavable protective group is described by Waldmann et al. in Angew. Chem. 107 (1995) 2425–2428.

Elmore et al. describe a first enzymatically cleavable linker for solid-phase peptide synthesis (J. Chem. Soc., Chem. Commun. 14 (1992) 1033–1034) which can be cleaved off the support under mild conditions. Schuster et al. describe another enzymatically cleavable linker for solid-phase syntheses of sugars (J. Am. Chem. Soc. 116 (1994) 1135–1136 and U.S. Pat. No. 5,369,017).

The disadvantage of both methods is that parts of the linker always remain in the product after the enzymatic cleavage. In addition, both methods are greatly restricted with regard to the linker-cleaving enzymes; thus Elmore uses calf spleen phosphodiesterase for the cleavage, and Schuster et al. describe serine proteases for the cleavage.

SUMMARY OF THE INVENTION

It is an object of the present invention to develop a linker which can be cleaved under mild conditions and, does not have the abovementioned disadvantages and makes possible a wide range of solid-phase organic syntheses.

We have found that this object is achieved by an enzymatically cleavable linker which is bound to a solid phase and on which organic compounds are synthesized via a functional group, wherein the linker contains a recognition site for a hydrolytic enzyme and is fragmented by reaction with the enzyme in such a way that no parts of the linker molecule remain in the synthesized product, and wherein the recognition site for the enzyme and the site at which the synthetic product is liberated by fragmentation of the linker are different.

The invention additionally relates to the preparation of the linkers and to their use.

DETAILED DESCRIPTION OF THE INVENTION

A preferred linker has the formula I

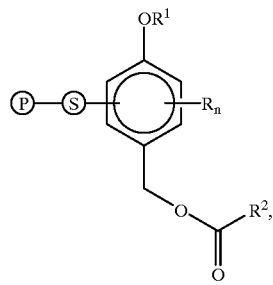

(I)

in which the variables and substituents have the following meanings:

(P) a solid phase (S) a spacer with a length equivalent to 1 to 30 methylene groups R hydrogen or a radical which is inert under the reaction conditions or two adjacent inert radicals R which together form an aromatic, heteroaromatic or aliphatic ring $R^1$ substituted or unsubstituted $C_1$–$C_{20}$-alkyl, $C_3$–$C_{20}$-alkenyl, $C_3$–$C_6$-alkynyl, $C_1$–$C_{20}$-alkylcarbonyl, $C_1$–$C_{20}$-alkylphosphoryl, $C_3$–$C_{20}$-alkenylcarbonyl, $C_3$–$C_6$-alkynylcarbonyl, $C_3$–$C_{20}$-alkenylphosphoryl, $C_3$–$C_6$-alkynylphosphoryl, $C_3$–$C_{20}$-cycloalkyl, $C_3$–$C_{20}$-cycloalkylcarbonyl, $C_3$–$C_{20}$-cycloalkylphosphoryl, aryl, arylcarbonyl, arylphosphoryl, hetaryl, hetarylcarbonyl, hetarylphosphoryl, glycosyl, substituted or unsubstituted amino acids or peptides $R^2$ a nucleofugic group n 1 or 2.

Linkers according to the invention are linkers which contain a recognition site for a hydrolytic enzyme and are fragmented by reaction with the enzyme in such a way that the linker is completely eliminated from a synthesized product which is bound via the linker to the solid phase, i.e. no parts of the linker molecule remain in the synthesized product.

The linker is preferably eliminated from the product synthesized on the solid phase with elimination of $CO_2$.

A recognition site for an enzyme means a linkage which can be cleaved by a hydrolytic enzyme. Examples of linkages which can be cleaved by hydrolytic enzymes are ester, amide, ether, phosphoric ester or glycoside linkages.

Suitable enzymes for cleaving the linker according to the invention under mild conditions are hydrolytic enzymes such as lipases, esterases, amidases, proteases, peptidases, phosphatases, phospholipases, peroxidases or glycosidases. Preferred enzymes are selected from the group of lipases, esterases, amidases, proteases or glycosidases, particularly preferably lipases, esterases or glycosidases.

Linkers according to the invention are depicted by way of example in formula IV (Scheme A).

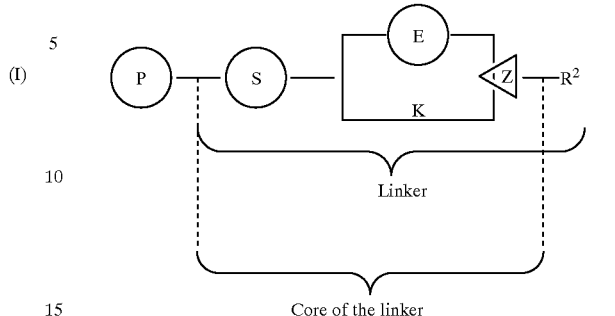

(IV)

where the substituents and variables have the following meanings:

(P) a solid phase (S) a spacer with a length equivalent to 1 to 30 methylene groups (E) recognition site for a hydrolytic enzyme (K) central linker structure (Z) functional group on which the product is liberated $R^2$ nucleofugic group via which synthesis of the products on the linker takes place.

There is connection via the central linker structure of the enzyme recognition site (E), the solid phase (P) via the spacer (C) and the site (Z) at which the product is liberated.

To construct the linker it is necessary for at least three functionalities to be present in the molecule or to be introducable into the central molecule. The enzyme recognition site, the solid phase and the functional group on which the product is linked to the linker are connected via the functionalities. Beyond this, there are no restrictions on the chemical structure of the central linker.

The central linker structure may consist of unsubstituted or substituted aliphatic, aromatic or heteroaromatic structures or combinations thereof. The central linker structure preferably contains aromatic structures, for example a phenyl or naphthyl ring.

Besides the solid phase, the spacer, the enzyme recognition site and the functional group at which the product is liberated (=core of the linker), the linker contains a nucleofugic group ($R^2$) via which the synthetic products are attached.

Mild and selective elimination of the synthetic products from the support material is made possible by the linker without the synthetic products being destroyed or altered.

Advantageous for the enzymatic elimination of the product from the linker are pH ranges of pH 2.0 to 10.0, preferably of pH 4.0 to 8.0, and temperature ranges of −10° C. to 100° C., preferably of 15° C. to 500° C. The elimination can take place in aqueous solution or in up to almost pure solvent with traces of water. Elimination with a solvent content of from 10 to 50% by weight is preferred.

To assemble the linker on a solid phase, the latter must if necessary be modified in a manner known to the skilled worker.

The linker is linked to the solid phase via an ester, ether, amide, amine, sulfide or phosphate linkage, depending on which solid phase is to be used.

Linkage to the solid phase moreover takes place in a conventional way.

Thus, for example, attachment to Merrifield resin or to 2-chlorotrityl-resin of compounds with free hydroxyl groups is described in P.M. Worster et al. (Angew. Chem. Int. Ed. Engl. 18 (1979) 221) and in C. Chen et al. (J. Am. Chem. Soc. 116 (1994) 2661–2662).

Attachment via an amino linkage is described, for example in M. Cardno et al. (J. Chem. Soc., Chem. Commun. 1995, 2163 ff) for 2-chlorotrityl-resin, in E. Bayer (Angew. Chem. 103 (1991) 117) for Nova Syn® TG carboxyl-resin, in J. R. Hanske et al. (Tetrahedron Lett., 36 (1995), 1589–1592) for Wang or Tentagel® S PHB resin.

Attachment to the support via thiol groups is described, for example, for Merrifield resin in Reynolds et al. (U.S. Pat. No. 5,324,483).

The examples of attachment which are mentioned here and are well known to the skilled worker are given here only as examples of reactions, and other possibilities for attachment are known to the skilled worker (Lit. Calbiochem-Novabiochem—The Combinatorial Chemistry Catalog Feb. 1996, 1–26 and S1–S24).

In the preferred linker of the formula I, fragmentation of the linker is induced by cleavage of the enzyme recognition site by, for example, enzymes such as lipases, esterases, amidases, proteases or glycosidases. The enzymatic cleavage of the linker initially results in a phenolate which spontaneously decomposes into a quinone methide which is linked to the solid phase and $CO_2$. This liberates the product containing no linker residues.

The preferred linker of the formula I is a phenylogous acetal. Other linkers according to the invention may also contain vinylogous or normal acetals derived therefrom (see reaction 2).

Advantageous linkers according to the invention fragment after enzymatic cleavage to form, for example, a lactam or lactone and thus liberate the product without linker residues. The following reactions 1 and 2 are intended to illustrate these general principles of fragmentation by way of example:

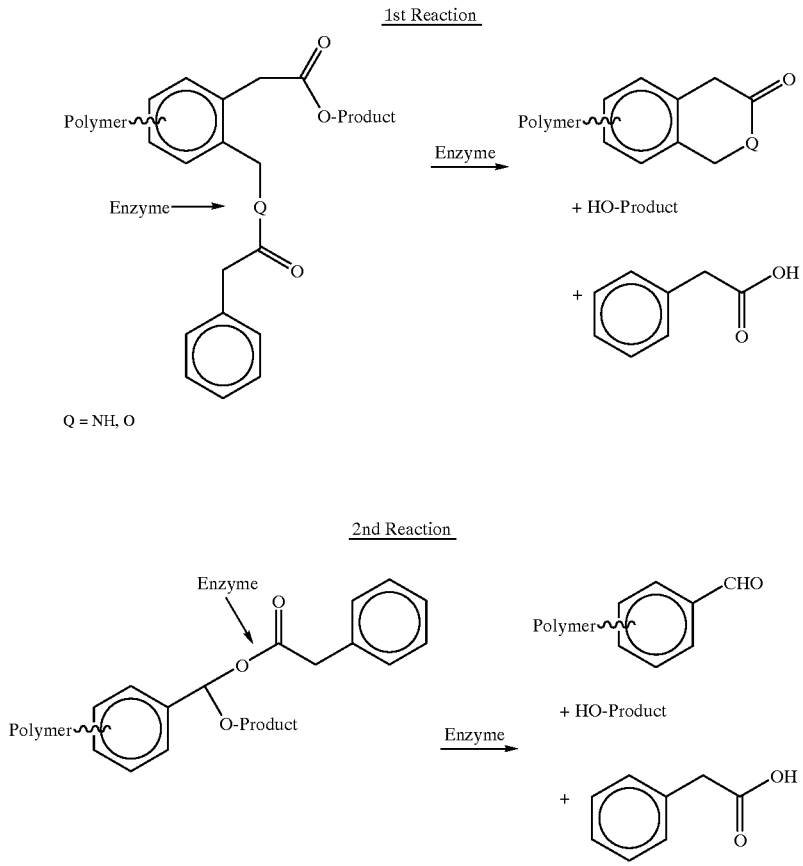

Q = NH, O

These principles of fragmentation illustrated in reactions 1 and 2 are not restricted to the enzyme recognition sites shown therein, such as lipases or amidases.

Linkers according to the invention are distinguished by a spatial distance between the enzyme recognition site and the site at which the product is liberated by fragmentation of the linker, i.e. enzyme recognition site and the site at which the product is liberated are different. This very substantially precludes steric impairment of the enzymatic reaction by the substrate. The distance between the enzyme recognition site and the site at which the product is liberated is, expressed in methylene group units, advantageously from 2 to 8 methylene units, preferably 4 to 8 methylene units.

The linkers according to the invention are completely eliminated from the product by a large number of enzymes under mild conditions, and remain on the solid phase.

It is possible in principle to use as solid phase (P) for the linkers according to the invention all the supports as are known, for example, from solid-phase peptide synthesis or nucleic acid synthesis.

Supports which can be used may consist of a large number of materials as long as they are compatible with the synthetic combinatorial chemistry used and with the attachment of the linker to the solid phase. The size of the supports can vary within wide limits depending on the material. Particles in the range from 1 µm to 1.5 cm are preferably used as support, and particles in the range from 1 µm to 150 µm are particularly preferred in the case of polymeric supports. However, gels are also suitable.

The shape of the supports is as desired, and spherical particles are preferred. The supports may have a homogeneous or heterogeneous size distribution, but homogeneous particle sizes are preferred.

It is also possible, where appropriate, for mixtures of different particles to be used.

Support materials of little or no compressibility are preferred to compressible materials if, for example, the product bound to the support is to be removed, for example, by centrifugation, or a product is to be synthesized in flow reactors, i.e. the supports should advantageously have a certain stability to pressure and favorable sedimentation characteristics.

It is also advantageous when mechanical stress is prolonged for the supports to have favorable resistance to abrasion.

Advantageous supports should be porous materials such as sintered glass, sintered metals, porous ceramics or resins with a large internal surface area in a range from 5 to 2000 $m^2/g$ of support material, preferably 40 to 800 $m^2/g$, particularly preferably 50 to 500 $m^2/g$. The pore diameter of the materials should advantageously be chosen so that there are no limitations on mass transfer through diffusion or through active mass flow. The pore diameter is expediently from 10 nm to 500 nm, preferably from 30 nm to 200 nm.

The support materials should advantageously have a pore volume which is as large as possible (>1 ml/g of support material).

It is possible to use natural, inorganic or organic materials.

Examples of suitable solid phases (P) are functionalized particles selected from the group of ceramics, glass, latex, crosslinked polystyrenes, crosslinked polyacrylamides or other resins, natural polymers, gold, colloidal metal particles, silica gels, aerogels or hydrogels.

The linkers can be linked on the surface of the solid phase or in the interior of the solid phase or to both.

Latices mean colloidal dispersions of polymers in aqueous media.

These may be natural or synthetic latices or microlatices which have been prepared, for example, by emulsion polymerization of suitable monomers or by dispersing polymers in suitable solvents.

Crosslinked polystyrenes, crosslinked polyacrylamides and other resins mean, for example, polyacrylamide, polymethacrylamide, poly(hydroxyethyl methacrylate), polyamide, polystyrene, (meth)acrylate copolymers of, for example, (meth)acrylic acid, (meth)acrylic esters and/or itaconic acid, crotonic acid, maleic acid, PU foams, epoxy resins or other copolymers.

Examples of natural polymers or supports which may be mentioned are agarose, cellulose, alginate, chitosan, dextran, levan, xanthan, collagen, gellan, X-carrageenan, agar, pectin, ramanian, wood chips, microcrystalline cellulose, hexosamines or gelatin.

Supports which are likewise suitable are diatomaceous earth, kieselguhr, metal oxides or expanded clay.

Selection of the suitable support depends on the chemistry for attaching the linker to the solid phase and on the synthetic chemistry carried out subsequently. Groups incompatible with this chemistry are protected in a manner known to the skilled worker.

A part is also played in the selection of the suitable support by the fact that the support advantageously contains no groups or ions or other molecules which damage the enzyme used for eliminating the linker, and, where appropriate, these groups should be removed, protected, washed out or inactivated before or after the synthesis.

If this is impossible, use of a larger amount of enzyme may, where appropriate, overcome this problem.

In order to make it possible to attach the linker to the solid phase, a support which is suitably functionalized or can be functionalized in a manner known to the skilled worker will be selected.

Examples of suitable and preferred supports are chlorobenzyl-resin (Merrifield resin), Rink resin (Novabiochem), Sieber resin (Novabiochem), Wang resin (Bachem) Tentagel resins (Rapp-Polymere), Pega resin (Polymer Laboratories) or polyacrylamides. 9-Fmoc-amino-3-xanthenyloxy-Merrifield resin, phenylalaninol-2-chlorotrityl-resin, prolinol-2-chlorotrityl-resin, 5-nitroanthranilic acid-2-chlorotrityl-resin or hydrazine-2-chlorotrityl-resin.

Suitable and particularly preferred supports are supports with an amino group for attachment of the linker, such as polyacryl-amides, Pega resins, Tentagel® S-$NH_2$, aminomethyl-polystyrene, 4-methylbenzhydrylamine-resin (=MBHA); Novasyn® TG amino-resin, 4-(2'4'-dimethoxyphenyl-Fmoc-aminomethyl) phenoxyacetamidonor-leucylaminomethyl-resin [sic], 4-(2'4'-dimethoxyphenyl-Fmoc-aminomethyl) phenoxyacetamidonorleucyl-MBHA-resin [sic], 4-(2'4'-dimethoxyphenyl-Fmoc-aminomethyl)phenoxy-resin [sic], 9-Fmoc-amino-3-xanthenyloxy-Merrifield resin, phenylalaninol-2-chlorotrityl-resin, prolinol-2-chlorotrityl-resin, 5-nitro-anthranilic acid-2-chlorotrityl-resin or hydrazine-2-chloro-trityl-resin.

The spacer (S) in the compounds of the general formulae I and II means a spacer with a length equivalent to 1 to 30 methylene groups. The spacer can have any desired structure. The distance between the central linker structure and the solid phase is advantageously adjusted by the length of the spacer so that the linker can be optimally cleaved by the enzymes used.

If the reactive group via which the spacer is linked to the solid phase is already at a spatial distance from the solid phase, as is the case, for example, with Nova Syn® TG bromo-resin (=slightly crosslinked polystyrene resin with polyethylene glycol tails of 3000–4000 MW terminally functionalized with bromine) via polyethylene glycol chains or with Rink amides MBHA-resin [=4(2'4'-dimethoxyphenyl-Fmoc-aminomethyl)-phenoxyacetamidonorleucyl-4-methylbenzhydrylamine-resin] [sic], the spacer can advantageously be chosen to be correspondingly shorter. If this reactive group is directly on the support, the spacer should advantageously be chosen to be correspondingly longer. The spacer can have any desired structure, which is of minor importance. The groups present in the structure and in the substituents which are present where appropriate should, however, expediently not interfere with the synthetic chemistry which is carried out.

The basic framework or backbone of the spacer can consist, for example, of an unsubstituted or substituted polymethylene chain which, in place of one or more methylene groups, contains radicals such as heteroatoms such as N, O, S, P, Sn or Si or unsubstituted or substituted aliphatic or aromatic rings or ring systems, which may, where appropriate, contain further heteroatoms such as N, S or O.

Combinations of said radicals can also be present in the basic framework of the spacer.

The spacer is linked to the solid phase by at least one linkage selected from the group of ester, ether, amide, amine, sulfide or phosphate linkages.

Meanings which may be mentioned for radical R in the compounds of the formula I and II are hydrogen or a radical which is inert under the reaction conditions, or two adjacent inert radicals R which may together form an aromatic, heteroaromatic or aliphatic ring. Inert radicals mean any suitable aliphatic, aromatic or heteroaromatic radicals or mixtures of these radicals.

Examples of aliphatic radicals which may be mentioned are unsubstituted or substituted $C_1$–$C_8$-alkyl, $C_2$–$C_8$-alkynyl, $C_3$–$C_6$-alkynyl or cycloalkyl.

Alkyl radicals which may be mentioned are branched or unbranched $C_1$–$C_8$-alkyl chains such as methyl, ethyl, n-propyl, 1-methylethyl, n-butyl, 1-methylpropyl, 2-methylpropyl, 1,-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl.

Alkenyl radicals which may be mentioned are branched or unbranched $C_3$–$C_8$-alkenyl chains such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl or 7-octenyl.

Alkynyl means $C_3$–$C_6$-alkynyl radicals such as prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl or 4-methyl-pent-2-yn-5-yl.

Cycloalkyl radicals which may be mentioned are branched or unbranched $C_3$–$C_{10}$-cycloalkyl chains with 3 to 7 carbon atoms in the ring, which may contain heteroatoms such as S, N or O or ring system such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl oder cyclodecyl.

Suitable substituents are one or more inert substituents such as halogen, alkyl, aryl, alkoxy, benzyloxy or benzyl.

Aromatic radicals mean single or fused ring systems. Phenyl and naphthyl are the preferred radicals.

Heteroaromatic radicals are advantageously single or fused aromatic ring systems with one or more heteroaromatic 3- to 7-membered rings. The heteroatoms which may be present are one or more nitrogen, sulfur and/or oxygen atoms in the ring or ring system.

Suitable substituents on the aromatic or heteroaromatic radicals are one or more substituents such as halogen, alkyl, aryl, alkoxy, benzyloxy or benzyl.

Two adjacent radicals R may together form an aromatic, heteroaromatic or aliphatic, unsubstituted or substituted, 4- to 8-membered ring.

The variable n in the compounds of the formulae I and II has the meaning of one or two.

Radicals which may be mentioned for $R^1$ in the compounds of the formulae I and II are substituted or unsubstituted $C_1$–$C_{20}$-alkyl, $C_3$–$C_{20}$-alkenyl, $C_3$–$C_6$-alkynyl, $C_1$–$C_{20}$-alkylcarbonyl, $C_1$–$C_{20}$-alkylphosphoryl, $C_3$–$C_{20}$-alkenylcarbonyl, $C_3$–$C_6$-alkynylcarbonyl, $C_3$–$C_{20}$-alkenylphosphoryl, $C_3$–$C_6$-alkynylphosphoryl, $C_3$–$C_{20}$-cycloalkyl, $C_3$–$C20$-cycloalkylcarbonyl, $C_3$–$C_{30}$-cycloalkylphosphoryl, aryl, arylcarbonyl, arylphosphoryl, hetaryl, hetarylcarbonyl, hetarylphosphoryl, glycosyl, substituted or unsubstituted amino acids or peptides, where alkyl is branched or unbranched $C_1$–$C_{20}$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosenyl [sic];

alkenyl is branched or unbranched $C_3$–$C_{20}$-alkenyl such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl- 4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl, decenyl, undecenyl, dodecenyl, tridecenyl, tetradecenyl, pentadecenyl, hexadecenyl, heptadecenyl, octadecenyl, nonadecenyl or eicosenyl;

alkynyl is branched or unbranched $C_2$–$C_6$-alkynyl such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl or 4-methyl-pent-2-yn-5-yl;

alkylcarbonyl is branched or unbranched $C_1$–$C_{20}$-alkylcarbonyl with alkyl groups as defined above for $R^1$, which are linked to the framework via a carbonyl group [—(C=O)—];

alkylphosphoryl is branched or unbranched $C_1$–$C_{20}$-alkylphosphoryl with alkyl groups as defined above for $R_1$, which are linked to the framework via a phosphoryl group [—O—P(O)(OH)—];

alkenylcarbonyl is branched or unbranched $C_3$–$C_{20}$-alkenylcarbonyl with alkenyl groups as defined above for $R^1$, which are linked to the framework via a carbonyl group [—(C=O)—];

alkenylphosphoryl is branched or unbranched $C_3$–$C_{20}$-alkenylphosphoryl with alkenyl groups as defined above for $R^1$, which are linked to the framework via a phosphoryl group [—O—P(O)(OH)—);

alkynylcarbonyl is branched or unbranched $C_3$–$C_6$-alkynylcarbonyl with alkynyl groups as defined above for $R^1$, which are linked to the framework via a carbonyl group [—(C=O)—];

alkynylphosphoryl is branched or unbranched $C_3$–$C_6$-alkynylphosphoryl with alkynyl groups as defined above for $R^1$, which are linked to the framework via a phosphoryl group (—O—P(O)OH—];

cycloalkyl is branched or unbranched $C_3$–$C_{20}$-cycloalkyl chains with 3 to 7 carbon atoms in the ring, which may contain heteroatoms such as S, N or O or ring systems such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl;

cycloalkylcarbonyl is branched or unbranched $C_3$–$C_2$-cycloalkylcarbonyl chains with 3 to 7 carbon atoms in the ring, which may contain heteroatoms such as S, N or O or ring systems such as cyclopropylcarbonyl, cyclobutylcarbonyl, cyclopentylcarbonyl, cyclohexylcarbonyl, cycloheptylcarbonyl, 1-methylcyclopropylcarbonyl, 1-ethylcyclopropylcarbonyl, 1-propylcyclopropylcarbonyl, 1-butylcyclopropylcarbonyl, 1-pentylcyclopropylcarbonyl, 1-methyl-1-butylcyclopropylcarbonyl, 1,2-dimethylcyclopropylcarbonyl, 1-methyl-2-ethylcyclopropylcarbonyl, cyclooctylcarbonyl, cyclononylcarbonyl or cyclodecylcarbonyl;

cycloalkylphosphoryl is branched or unbranched $C_3$–$C_{20}$-cycloalkylphosphoryl chains with 3 to 7 carbon atoms in the ring, which may contain heteroatoms such as S, N or O or ring systems such as cyclopropylphosphoryl, cyclobutylphosphoryl, cyclopentylphosphoryl, cyclohexylphosphoryl, cycloheptylphosphoryl, 1-methylcyclopropylphosphoryl, 1-ethylcyclopropylphosphoryl, 1-propylcyclopropylphosphoryl, 1-butylcyclopropylphosphoryl, 1-pentylcyclopropylphosphoryl, 1-methyl-1-butylcyclopropylphosphoryl, 1,2-dimethylcyclopropylphosphoryl, 1-methyl-2-ethylcyclopropylphosphoryl, cyclooctylphosphoryl, cyclononylphosphoryl or cyclodecylphosphoryl;

aryl such as phenyl or naphthyl;

arylcarbonyl such as phenylcarbonyl or naphthylcarbonyl;

arylphosphoryl such as phenylphosphoryl or naphthylphosphoryl;

hetaryl, hetarylcarbonyl or hetarylphosphoryl which [lacuna] in their hetaryl moiety aromatic mono- or polycyclic radicals which, besides carbon ring members, may additionally contain one to four nitrogen atoms or one to three nitrogen atoms and one oxygen or one sulfur atom or one oxygen or one sulfur atom;

glycosyl, mono-, di- or oligosaccharides such as glucose, galactose, mannose, fructose, fucose, N-acetyl-D-glucosamine, maltose, lactose, chitobiose, cellobiose or oligosaccharides in all their stereoisomeric forms (α- or β-configuration) and all their possible linkage types [α-(1,3)-, α-(1,4)-, α-(1,6)-, β-(1,2)-, β-(1,3)-, β-(1,4)-, β-(1,6)] as homo- or heteromers, it being necessary that the sugar linking to the framework be recognized by an endo- or exoglycosidase or mixtures thereof, and the glycosidic linkage be cleavable.

Substituted or unsubstituted amino acids or peptides mean natural or unnatural amino acids or peptides which contain the latter. The amino acids and peptides attached to the framework must be chosen so that they can be eliminated by an exo- or endopeptidase or an exo- or endoprotease or mixtures of these.

All said radicals $R^1$ may, where appropriate, carry other substituents as long as they do not block the recognition site for the enzyme.

$R^2$ in the compounds of the formulae I and III is a nucleofugic group which permits attachment of other suitable radicals via a nucleophilic group to the linker according to the invention and thus makes subsequent combinatorial chemistry on the solid phase possible.

Nucleofugic groups which may be mentioned are leaving groups such as halogen such as Br, Cl or F or groups such as

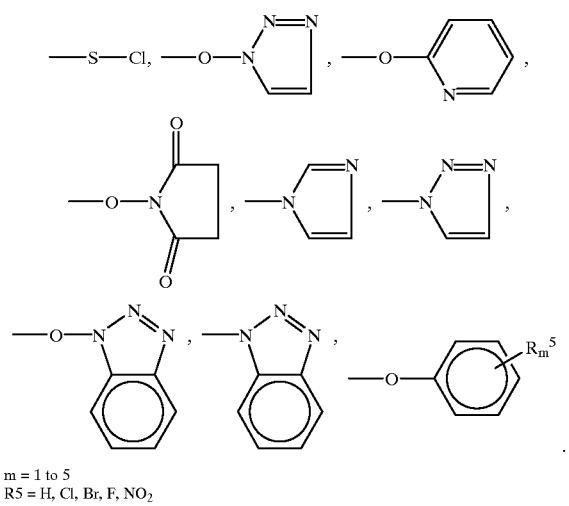

m = 1 to 5
R5 = H, Cl, Br, F, NO$_2$

Y in the compounds of the formula III has the meaning specified for R$^2$ and can be identical to or different from R$^2$.

X in the compounds of the formula II is one of the following groups —(C=O)—O—, —O—, -NR$^3$—, —S—, —OPO(OR$^4$)—O—, where R$^3$ and R$^4$ are, independently of one another, hydrogen or C$_1$–C$_8$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl.

The linker is linked via the group XH to the solid phase (P). All groups which make this linkage possible are suitable for the synthesis.

The linker which is linked according to the invention to the solid phase is advantageously assembled in a reaction sequence which is depicted hereinafter by way of example for Tentagel® S-NH$_2$ as suppport and two different linker structures (Scheme I and II).

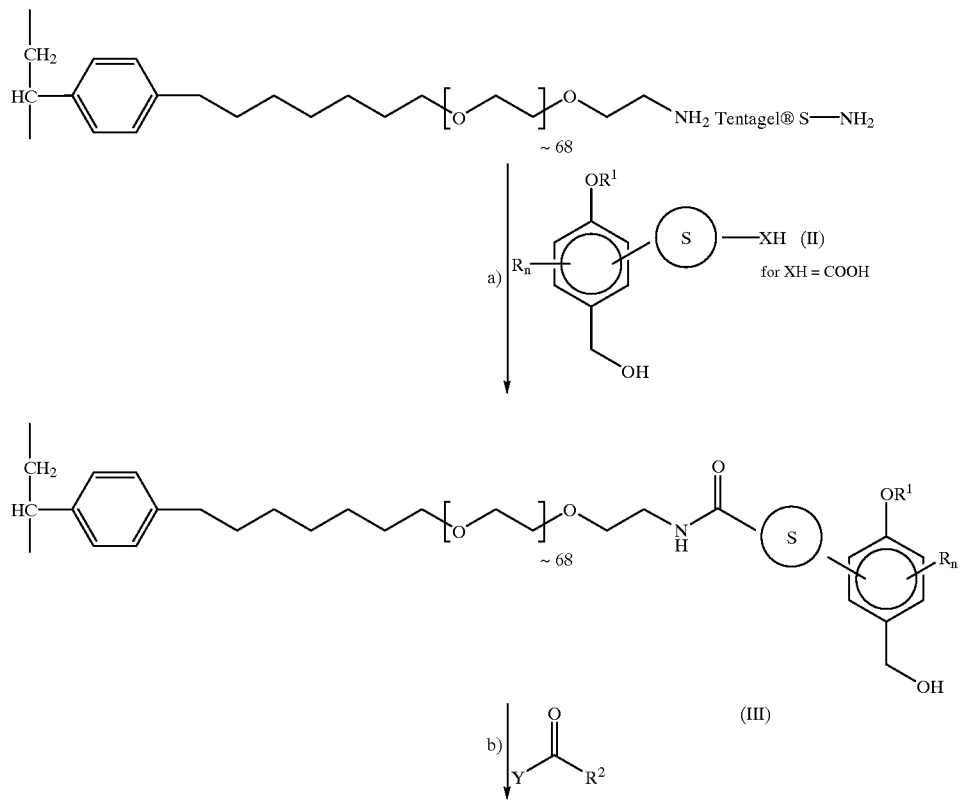

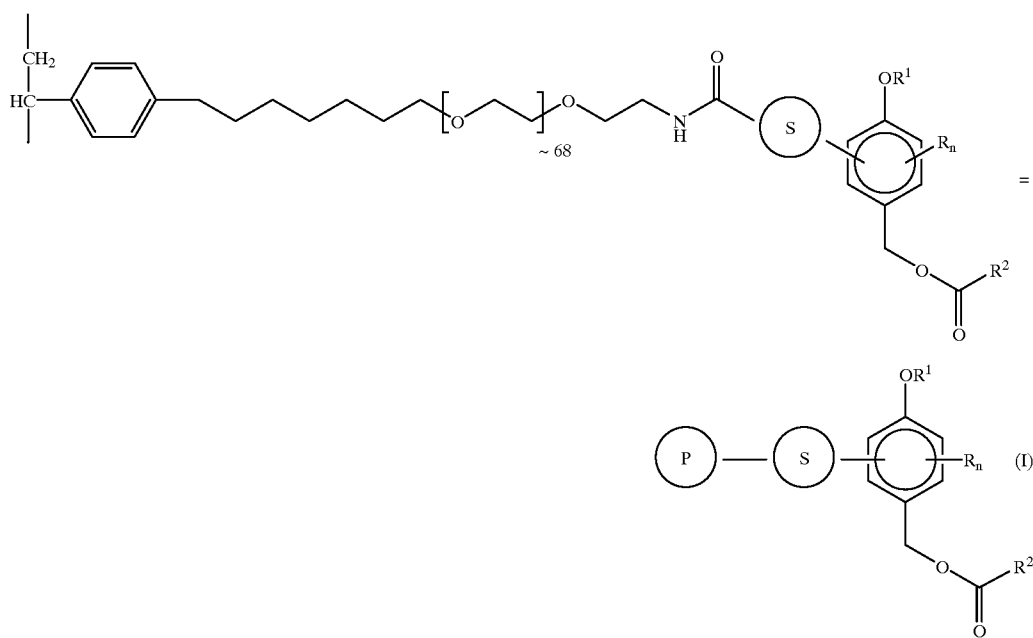

The attachment reactions a) between the support and compounds of the formula II are carried out, for example when XH is a carboxyl radical, in solvent with the aid of, for example, diisopropylcarbodiimide (=DIC). Other coupling reagents suitable for forming this amide linkage are, for example, TBTU, HBTS, BOP or PYBOP (Lit.: Int. J. Peptide Prot. Rev. 35, 1990: 161–214). Suitable solvents are aprotic, nonpolar or polar solvents, for example dimethylformamide (DMF), methylene chloride ($CH_2Cl_2$), dimethyl sulfoxide (DMSO) or tetrahydrofuran (THF). It is possible to use single solvents or mixtures. The hydroxymethylene group in the formula II must be protected where appropriate for the attachment to the linker.

Reaction b) is carried out to introduce the nucleofugic group which makes it possible to attach other molecules, which are then subsequently derivatized combinatorially, into the linker.

Reaction b) is advantageously carried out with phosgene or phosgene equivalents in an aprotic, polar or nonpolar solvent such as $CH_2Cl_2$, DMF, DMSO, THF, toluene, acetonitrile or mixtures thereof.

Y and $R^2$, and the other radicals mentioned in the formulae I to III in Scheme I have the abovementioned meanings.

Both reactions are carried out at a temperature in the range from –20° C. to +120° C., preferably from 0° C. to +60° C., and reaction b) can, where appropriate, be carried out in the presence of catalytic amounts of DMAP (=4-dimethylaminopyridine).

Scheme II

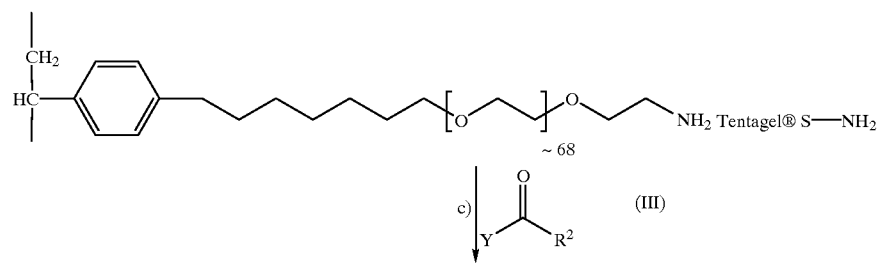

-continued

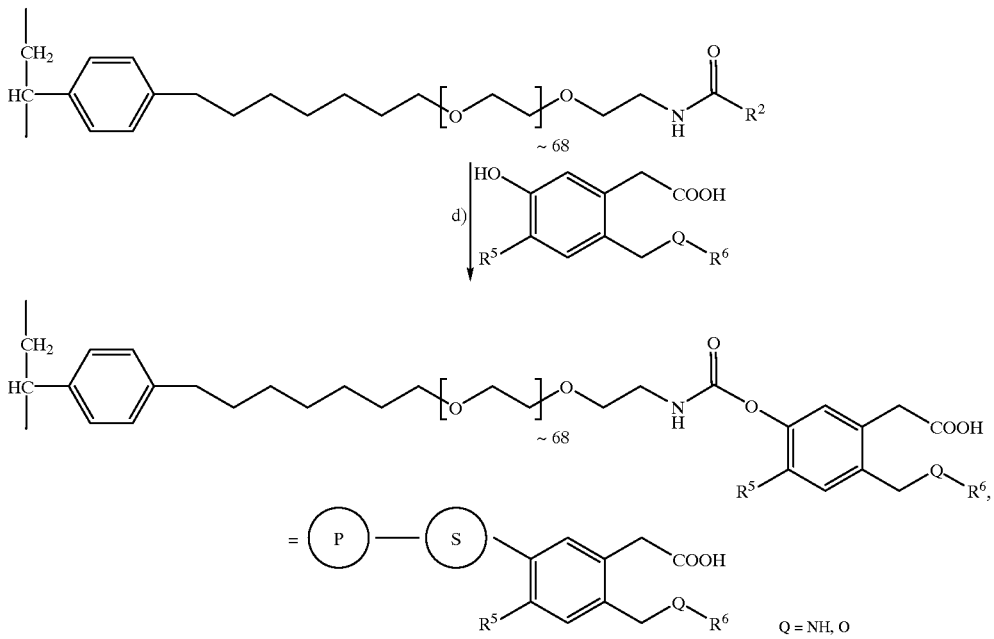

To attach the linker to the solid phase or the support (see Scheme II), the latter is initially functionalized. To do this, the support is reacted with a compound of the formula III (see reaction c) where the radicals $R^2$ and Y have the abovementioned meanings. All phosgene equivalents are suitable for functionalizing the support. They result in introduction of a nucleofugic group, via which the linker is linked to the support.

Reaction c) is carried out in aprotic, polar or nonpolar solvents such as $CH_2Cl_2$, DMF, DMSO, THF, toluene, acetonitrile or mixtures thereof.

The reaction is carried out at a temperature in the range from −20° C. to +120° C., preferably from 0° C. to +60° C., and the reaction can, where appropriate, be carried out in the presence of catalytic amounts of DMAP. The linker is finally linked to the support via the nucleofugic group $R^2$ (reaction d).

Reaction d) is carried out in aprotic, polar or nonpolar solvents such as $CH_2C_2$, DMF, DMSO, THF, toluene, acetonitrile or mixtures thereof.

The reaction is carried out in the presence of a tertiary amine base such as triethylamine- [sic] or diisopropylethylamine and catalytic amounts of DMAP. Reaction d) is carried out at a temperature in the range from 0° C. to +120° C., preferably from 20° C. to 80° C.

The radicals $R^5$, $R^6$ and Q have the following meanings:

$R^5$ hydrogen, OH, $NO_2$, unsubstituted or substituted $C_1$–$C_8$-alkyl, $C_1$–$C_8$-alkoxy, $C_3$–$C_{10}$-cycloalkyl, $C_3$–$C_{10}$-cycloalkyloxy, $R^6$ substituted or unsubstituted $C_1$–$C_{20}$-alkyl, $C_3$–$C_{20}$-alkenyl, $C_3$–$C_6$-alkynyl, $C_1$–$C_{20}$-alkylcarbonyl, $C_1$–$C_{20}$-alkylphosphoryl, $C_3$–$C_{20}$-alkenylcarbonyl- [sic], $C_3$–$C_6$-alkynylcarbonyl- [sic], $C_3$–$C_{20}$-alkenylphosphoryl- [sic], $C_3$–$C_6$-alkynylphosphoryl- [sic], $C_3$–$C_{20}$-cycloalkyl- [sic], $C_3$–$C_{20}$-cycloalkylcarbonyl-[sic], $C_3$–$C_{20}$-cycloalkylphosphoryl-[sic], aryl-[sic], arylcarbonyl-[sic], arylphosphoryl-[sic], hetaryl-[sic], hetarylcarbonyl-[sic], hetarylphosphoryl-[sic], glycosyl-[sic], substituted or unsubstituted amino acids or peptides Q NH or O.

The radical $R^6$ must be selected so that recognition sites which can be recognized and cleaved by enzymes are produced. Linkages produced by suitable choice of the radical $R^6$, and meeting the abovementioned criterion are, for example, ester, ether, amide, phosphoric ester and glycoside linkages. Enzymes which cleave these linkages are, for example, hydrolytic enzymes such as lipases, esterases, amidases, proteases, peptidases, phosphatases, phospholiphases [sic], peroxidases or glycosidases.

The advantage of the linker according to the invention and of the process according to the invention is that the linker is eliminated simply and completely from the product.

The linker according to the invention makes a wide range of subsequent synthetic chemistry possible, e.g. construction of a substance library in combinatorial chemistry, which can, where appropriate, be automated. The linker according to the invention can be used advantageously for solid-phase syntheses.

The following examples serve to illustrate the invention further without restricting it in any way.

EXAMPLE 1

Preparation of 2-acetoxy-5-methylbenzoic acid

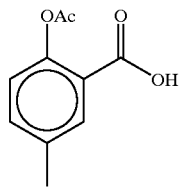

1 g of 5-methylsalicylic acid (6.58 mmol) and 1.83 ml of tri-ethylamine (2 equivalents) were dissolved in 80 ml of ethyl acetate. At 0° C., 0.94 ml of acetyl chloride (2 equivalents) was added dropwise, and the mixture was then stirred at 23° C. for 1 h. The precipitated salts are [sic] filtered off. 100 ml of 1M HCl were added to the filtrate, which was then stirred overnight. A homogeneous solution formed, and it was adjusted to about pH 4 with saturated NaHCO$_3$ solution. It was then extracted with chloroform, and the organic phase was washed with a little water and dried over MgSO$_4$. The solvent was substantially removed, and the crude product was recrystallized from hexane/ethyl acetate.

Yield: 1.21 g (95%) $^1$H-NMR (CDCl$_3$): 7.89 (d,J=2 Hz); 7.39 (dd,J=8 Hz, J'=2 HZ [sic]); 6.99 (d,J=8 Hz); 2.40 (s,3 H, —CH$_3$); 2.31 (s,3 H, —OAc).

EXAMPLE 2

Preparation of 2-acetoxy-5-bromomethylbenzoic acid

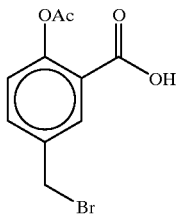

1 g of 2-acetoxy-5-methylbenzoic acid (5.16 mmol), 1.16 g of N-bromosuccinimide (1.25 equivalents) and 33 mg of azodiisobutyronitrile in 20 ml of absolute tetrachloromethane were cautiously heated while stirring under an argon atmosphere and refluxed while exposing to a sun lamp for 2.5 h. The mixture was then left to cool in an ice bath and filtered, and the filter cake was washed with n-pentane. The mass of crystals was taken up in CHCl$_3$ and washed with cold water. The organic phase was dried over MgSO$_4$ and concentrated. The crude product was further reacted immediately.

Yield: 1 g, 58% of title compound in addition to about 10% of 2-acetoxy-5-dibromomethylbenzoic acid (estimated from the $^1$H-NMR-spectrum) $^1$H-NMR (CDCl$_3$): 8.11 (d,J=2 Hz); 7.62 (dd,J=8 Hz, J'=2 Hz); 7.11 (d,J=8 Hz); 4.48 (s,2 H, —CH$_2$—); 2.33 (s,3 H, —OAc).

EXAMPLE 3

Preparation of 2-acetoxy-5-hydroxymethylbenzoic acid

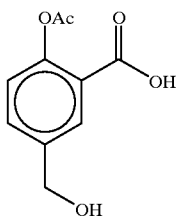

1 g of the crude product (2.99 mmol of 4) from Example 2 were mixed with 25.5 ml of dioxane and 30 ml of 0.1 N AgNO$_3$ solution and stirred at room temperature overnight. The mixture was then extracted several times with ethyl acetate, and the combined organic phases were dried over MgSO$_4$ and evaporated to dryness. Column chromatography with CHCl$_3$/methanol (5:1) afforded a yield of 389 mg (62%).

$^1$H-NMR (CDCl$_3$): 8.07 (d.J=2 Hz); 7.61 (dd,J=8 Hz, J'2 Hz); 7.12 (d,J=8 Hz); 4.73 (s,2 H, -CH$_2$); 2.32 (s,3 H, -OAc).

EXAMPLE 4

Attachment of the anchor building block 2-acetoxy5-hydroxy-methylbenzoic acid to Tentagel® S-NH$_2$

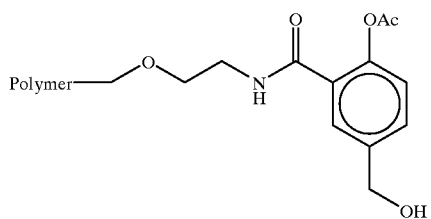

36.5 mg of 2-acetoxy-5-hydroxymethylbenzoic acid (1.2 equivalents) and 21.5 µl of diisopropylcarbodiimide (1.44 equivalents) were added to 500 mg of Tentagel® S-NH$_2$ (0.29 mmol of NH$_2$ groups/g) in 6 ml of absolute CH$_2$Cl$_2$. The reaction mixture was stirred at room temperature, and the resin was filtered off with suction. It was then washed successively on the filter three times each with absolute DMF, methanol and CH$_2$Cl$_2$, mixing by passing nitrogen through. The resin was dried under oil pump vacuum and the attachment protocol was repeated once, until the Kaiser test for free NH$_2$ groups was negative (E. Kaiser et al. Anal. Biochem. 1979, 34, 595).

FT-IR: 1766 cm.$^{-1}$ (—OAc), 1666 cm$^{-1}$ (—CONH—), 1540 cm$^{-1}$ (—NH—), 3100–3500 cm$^{31\ 1}$ (—OH).

EXAMPLE 5

Conversion to the chloroformic ester

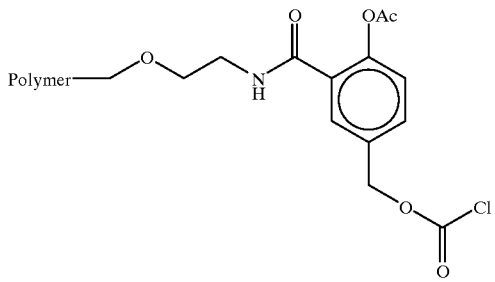

210 mg of the product obtained in Example 4 were introduced into 3.5 ml of absolute THF under argon, and 400 µl (about 12 equivalents) of a solution of phosgene in toluene (1.93 M) were added dropwise at 23° C. The suspension was stirred for 2 h and, after dropwise addition of a further 200 µl of the phosgene solution, stirred for a further 2 h. It was subsequently washed successively twice each with absolute THF, ethyl ether, THF and ethyl ether again, and the resin was dried under reduced pressure.

FT-IR: 1770,5 cm$^{-1}$ (—OAc and —COCl), 1666 cm$^{-1}$ (—CONH—), 1540 cm$^{-1}$ (—NH—).

EXAMPLE 6

Preparation of

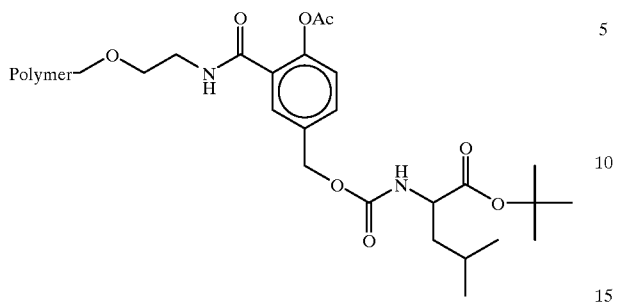

by coupling to leucine tert-butyl ester hydrochloride.

A solution, cooled in an ice-water bath, of 29 mg of leucine tert-butyl ester hydrochloride (4 equivalents) and 20 µl of triethylamine (about 5 equivalents) in 4 ml of absolute $CH_2Cl_2$ was slowly added at 0° C., under argon, to a suspension of 110 mg of the compound obtained in Example 5 in 2 ml of $CH_2Cl_2$. The suspension was stirred at 0° C. for 0.5 h and at 23° C. for 3 h. It was then washed successively in each case with absolute methanol, $CH_2Cl_2$, methanol and ethyl ether, and the resin was dried under reduced pressure.

FT-IR: 1776 $cm^{-1}$ (—OAc), 1724 $cm^{-1}$ (—OCONH—), 1666 $cm^{-1}$ (-CONH-), 1540 $cm^{-1}$ (—NH—).

EXAMPLE 7

Basic elimination of the leucine tert-butyl ester to determine the occupation density 6 mg of the coupling product from Example 6 were suspended in a solution of 200 µl of THF and 200 µl of saturated $NaHCO_3$ solution, pH 10.5, and the reaction mixture was shaken at 23° C. for about 30 min. It was then extracted with 200 µl of $CHl_3$, and the organic phase was quantified by GC-MS using a calibration plot. The proportion of leucine tert-butyl ester attached via the anchor building block to the polymeric support was 51% based on available $NH_2$ groups.

EXAMPLE 8

Enzymatic elimination of the leucine tert-butyl ester 27 mg of the coupling product from Example 6 were suspended in 1066 µl of phosphate buffer (0,1 M $Na_2HPO_4$, 0,2 M KI, pH 5) and 500 µl of methanol; 3 U of Mucor miehei lipase dissolved in 100 µl of the same buffer were added, and the mixture was incubated at 30° C. with shaking. The quinone methine [sic] produced as intermediate was trapped owing to the presence of iodide in the buffer solution. A further 100 µl of the lipase solution was added after 6 h and after 32 h. The incubation was stopped after 58 h. The reaction mixture was extracted with $CHCl_3$. The combined and dried organic phases were concentrated to 1 ml and quantified by GC-MS.

Yield: 42%

We claim:

1. A composition comprising a solid phase bound to an enzyme cleavable linker on which synthesis of an organic product takes place;
   said linker having a recognition site for a hydrolytic enzyme;
   said linker having a functional group to which an organic product is bound when synthesis of the product takes place;
   wherein said linker is fragmented upon reaction with the hydrolytic enzyme in such a way that no parts of the linker remain in the synthesized product;
   wherein the enzyme recognition site is different from a site where fragmentation occurs to liberate the synthesized product from the linker; and
   wherein said composition has the formula I,

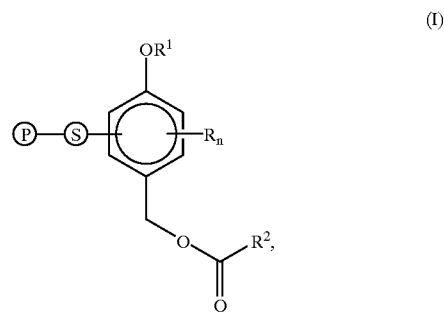

(I)

wherein
   Ⓟ is a solid phase;
   Ⓢ is a spacer with the length equivalent to 1 to 30 methylene groups linked to said solid phase via a linkage selected from the group consisting of ester, ether, amide, sulfide and phosphate;
   R is hydrogen or an inert radical, or two adjacent inert radicals R which together form an aromatic, heteroaromatic or aliphatic ring;
   n is 1 or 2;
   $R^1$ is substituted or unsubstituted $C_1$–$C_{20}$-alkyl, $C_3$–$C_{20}$-alkenyl, $C_3$–$C_6$-alkynyl, $C_1$–$C_{20}$-alkylcarbonyl, $C_1$–$C_{20}$-alkylphosphoryl, $C_3$–$C_{20}$-alkenylcarbonyl, $C_3$–$C_e$-alkynylcarbonyl, $C_3$–$C_{20}$-alkenylphosphoryl, $C_3$–$C_6$-alkynylphosphoryl, $C_3$–$C_{20}$-cycloalkyl, $C_3$–$C_{20}$-cycloalkylcarbonyl, $C_3$–$C_{20}$-cycloalkylphosphoryl, aryl, arylcarbonyl, hetaryl, hetarylcarbonyl, hetarylphosphoryl, glycosyl, substituted or unsubstituted amino acids or peptides; and
   $R^2$ is a nucleofugic group.

2. The composition defined in claim 1 wherein fragmentation of the linker eliminates $CO_2$.

3. The composition defined in claim 1 wherein the linker contains a recognition site for a hydrolytic enzyme selected from the group consisting of lipases, esterases, amidases, proteases, peptidases, phosphatases, phospholipases, peroxidases and glycosidases.

4. The composition defined in claim 1, where the solid phase is selected from the group consisting of ceramics, glass, latex, crosslinked polystyrenes, resins, natural polymers, gold, colloidal metal particles, silica gels, aerogel and hydrogel and said solid phase contains a functional group for attaching the solid phase to said linker.

5. The composition of claim 4 wherein the resin is a corsslinked polyacrylamide.

6. A process for preparing a composition comprising a solid phase having a bound enzyme cleavable linker on which synthesis of an organic product takes place, said linker containing a functional group to which a synthesized product is bound when synthesis of the product takes place, and a hydrolytic enzyme recognition site and a fragmentation site different from the recognition site such that the linker is fragmented at the fragmentation site upon reaction of the recognition site with a hydrolytic enzyme to release a synthesized product from the linker without the product containing any of the linker, said composition having formula I

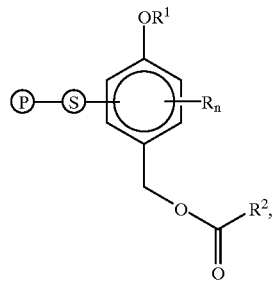

(I)

wherein
- ⓟ is a solid phase;
- Ⓢ is a spacer with the length equivalent to 1 to 30 methylene groups;
- R is hydrogen or an inert radical, or two adjacent inert radicals R which together form an aromatic, heteroaromatic or aliphatic ring;
- n is 1 or 2;
- $R^1$ is substituted or unsubstituted $C_1$–$C_{20}$alkyl, $C_3$–$C_{20}$-alkenyl, $C_3$–$C_6$-alkynyl, $Cl_1$–$C_{20}$-alkylcarbonyl, $C_1$–$C_{20}$-alkylphosphoryl, $C_3$–$C_{20}$-alkenylcarbonyl, $C_3$–$C_6$-alkynylcarbonyl, $C_3$–$C_{20}$-alkenylphosphoryl, $C_3$–$C_6$-alkynylphosphoryl, $C_3$–$C_{20}$-cycloalkyl, $C_3$–$C_{20}$-cycloalkylcarbonyl, $C_3$–$C_{20}$-cycloalkylphosphoryl, aryl, arylcarbonyl, hetaryl, hetarylcarbonyl, hetarylphosphoryl, glycosyl, substituted or unsubstituted amino acids or peptides; and
- $R^2$ is a nucleofugic group.

which process comprises the steps of linking to a solid phase via a spacer a compound of formula II

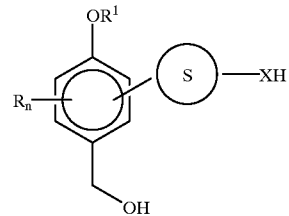

(II)

where X is COO, O $NR^3$, S, OPO($OR^4$)—O, where $R^3$ and $R^4$ are, independently of one another, hydrogen or $C_1$–$C_8$-alkyl, wherein said linking via said spacer is via a linkage selected from the group consisting of ester, ether, amide, amine, sulfide and phosphate, and subsequently reacting the product formed with a compound of the formula III

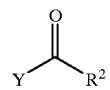

(III)

where Y and $R^2$ are identical or different nucleofugic groups.

* * * * *

UNITED STATES PATENT AND TRADEMARK OFFICE
CERTIFICATE OF CORRECTION

PATENT NO. : 6,271,345 B1
DATED : August 7, 2001
INVENTOR(S) : Waldmann et al.

It is certified that error appears in the above-identified patent and that said Letters Patent is hereby corrected as shown below:

<u>Column 22,</u>
Line 36, "$C_3$-$C_e$-alkynylcarbonyl" should be -- $C_3$-$C_6$-alkynylcarbonyl --.

Signed and Sealed this

Fifteenth Day of January, 2002

*Attest:*

*Attesting Officer*

JAMES E. ROGAN
*Director of the United States Patent and Trademark Office*